United States Patent [19]
Falkenstein et al.

[11] 3,970,600
[45] July 20, 1976

[54] STABLE, LIQUID SOLUTIONS OF ISOCYANURATE-POLYISOCYANATES CONTAINING AMIDE AND/OR ACYLUREA GROUPS

[75] Inventors: Georg Falkenstein, Neustadt; Richard Palm, Ludwigshafen; Dietrich Wolff, Schwetzingen, all of Germany

[73] Assignee: BASF Aktiengesellschaft, Ludwigshafen (Rhine), Germany

[22] Filed: Jan. 16, 1975

[21] Appl. No.: 541,639

[30] Foreign Application Priority Data
Jan. 28, 1974 Germany..................2403858

[52] U.S. Cl. .................. 260/77.5 NC; 252/182; 260/77.5 AC; 260/77.5 AT
[51] Int. Cl.$^2$ ................. C08G 18/79; C08G 18/71; C08G 18/20
[58] Field of Search............. 260/2.5 AW, 77.5 NC; 252/182

[56] References Cited
UNITED STATES PATENTS

| | | | |
|---|---|---|---|
| 3,652,424 | 3/1972 | Jackson et al............. | 260/77.5 NC |
| 3,723,363 | 3/1973 | Shaw.......................... | 260/2.5 AW |
| 3,879,316 | 4/1975 | Fishbein et al............. | 260/2.5 AW |

*Primary Examiner*—H.S. Cockeram
*Attorney, Agent, or Firm*—Johnston, Keil, Thompson & Shurtleff

[57] ABSTRACT

Stable, liquid, homogeneous solutions of isocyanurate-polyisocyanates containing amide and/or acylurea groups in monomeric diisocyanates and/or polyisocyanates which are free from amide, acylurea and/or isocyanurate groups, are obtained by reacting polybasic carboxylic acids with diisocyanates and/or polyisocyanates to give diisocyanates and/or polyisocyanates containing amide groups and/or acylurea groups, converting the diisocyanates and/or polyisocyanates containing amide and/or acylurea groups by trimerization and, optionally, polymerization, into isocyanurate-polyisocyanates containing amide and/or acylurea groups, and mixing the products with monomeric diisocyanates and/or polyisocyanates.

7 Claims, No Drawings

STABLE, LIQUID SOLUTIONS OF ISOCYANURATE-POLYISOCYANATES CONTAINING AMIDE AND/OR ACYLUREA GROUPS

The present invention relates to stable, liquid, homogeneous solutions of isocyanurate-polyisocyanates containing amide and/or acylurea groups in monomeric diisocyanates and/or polyisocyanates which are free from amide, acylurea and/or isocyanurate groups.

The trimerization of isocyanates in the presence of conventional trimerization catalyst is known.

According to German Published Application No. 2,153,107, tris-(isocyanatotoluyl)-isocyanurate/-toluylenediisocyanate complexes are obtained from the pure isomeric 2,4- and 2,6-toluylenediisocyanates or the isomer mixtures by addition of known trimerization catalysts, for example 1,3,5-tris-(3-dimethyl-aminopropyl)-hexahydrotriazine or 2,4,6-tri-dimethylaminomethyl)-phenol, and discontinuation of the reaction, or deactivation of the catalyst, by addition of acids or acid halides. In the pure state, the complexes are crystalline powders of one molecule of tri-(isocyanatotoluyl)-isocyanurate and 2 molecules of 2,4- and/or 2,6-toluylenediisocyanate, which have a narrow melting range. The complexes are relatively easily soluble in, e.g., carboxylic acid esters such as ethyl acetate, ketones, such as acetone, and aromatic hydrocarbons such as benzene or toluene, but are practically insoluble in aliphatic hydrocarbons such as n-hexane. The solubility in polyisocyanates which are free from isocyanurate groups, for example in 2,4- and 2,6-toluylenediisocyanate, and in the isomer mixtures, also varies, e.g., analysis of the unstable solutions which can be prepared from 2,4- and 2,6-toluylenediisocyanate-isocyanurates and 2,4- and 2,6-toluylenediisocyanate, and their mixtures, which are free from isocyanurate groups (the solutions containing up to 40% by weight of isocyanurates with isocyanate groups) shows that the complexes of 2,6-toluylenediisocyanate trimer are particularly difficult to dissolve in toluylenediisocyanate which is free from isocyanurate groups.

It has also been disclosed that polyurethane foams can be produced from polyhydroxylic compounds and/or polycarboxylic compounds and polyisocyanate solutions which are prepared from polyisocyanates containing more than one NCO group and at least one isocyanurate ring, and monomeric polyisocyanates.

According to German Pat. No. 1,027,394, monomeric diisocyanates or polyisocyanates are reacted with less than equivalent amounts of compounds containing one or more active hydrogen atoms, and are then trimerized. After mixing the resulting higher-molecular-weight polyisocyanates which contain isocyanurate groups with liquid monomeric polyisocyanates, the solutions are used to produce polyurethane foams containing isocyanurate groups. It is a disadvantage of the above solutions of polyisocyanates containing isocyanurate groups in monomeric polyisocyanates that though the solutions are clear at higher temperatures they rapidly deposit fine or coarse crystalline solids on cooling or storage and therefore are unsuitable for processing on foam-producing machinery using conventional methods.

According to German Published Application No. 2,052,028, some improvement in the shelf life of isocyanurate-polyisocyanate solutions in monomeric polyisocyanates is achieved by introducing urethane groups into the polyisocyanate containing isocyanurate groups, before or after the formation of the isocyanurate. These initially clear solutions, however, also deposit greater or lesser amounts of fine crystalline solids after storage for various periods at temperatures of from 20° to 25°; these solids can be identified as polyisocyanate trimer/monomer complexes.

We have found that, surprisingly, stable liquid isocyanuratepolyisocyanate solutions in monomeric polyisocyanates are obtained by using polyisocyanates containing at least one amide and/or acylurea group in the molecule as starting products for conversion to the isocyanurate.

Accordingly, the invention relates to stable, liquid solutions of isocyanurate-polyisocyanates containing amide and/or acylurea groups, which solutions contain:

A. From 5 to 40% by weight, based on the total weight of solution, of an isocyanurate-polyisocyanate with amide and/or acylurea groups, containing from 26 to 0.25% by weight of amide and/or acylurea groups, from 29 to 5% by weight of isocyanurate groups and from 40 to 20% by weight of free isocyanate groups. in each case based on the weight of the isocyanurate-polyisocyanate containing amide and/or acylurea groups, and B. from 95 to 60% by weight, based on the total weight of the solution, of a monomeric diisocyanate and/or polyisocyanate which is free from isocyanurate groups.

The invention further relates to a process for the production of stable, liquid solutions of isocyanurate-polyisocyanates containing amide and/or acylurea groups, as claimed in claim 1, wherein monomeric diisocyanates and/or polyisocyanates are modified with aliphatic and/or aromatic dicarboxylic acids of 4 to 20 carbon atoms used in such amounts that the ratio of NCO to COOH groups is from 200 : 1 to 2 : 1, the resulting diisocyanates and/or polyisocyanates containing amide and/or acylurea groups are partially trimerized and/or polymerized in the presence of a trimerization catalyst and after deactivation of the trimerization catalyst the resulting isocyanurate-polyisocyanates containing amide and/or acylurea groups are diluted with monomeric diisocyanates and/or polyisocyanates which are free from isocyanurate groups.

The stable solutions according to the invention have the following advantages:

Because polyisocyanates containing amide and/or acylurea groups are used for the trimerization, isocyanurate-polyisocyanates are obtained which in contrast to the trimeric polyisocyanates do not form complexes which are sparingly soluble in polyisocyanates which are free from isocyanurate groups. In addition, the use of polyisocyanates containing amide and/or acylurea groups for the manufacture of isocyanurate-polyisocyanates increases the average NCO-functionality of the products and lowers their toxicity, so that the products can be used for numerous types of applications; e.g., they can be used particularly advantageously to manufacture rigid foams. Finally, the isocyanurate-polyisocyanates modified with amide and/or acylurea groups give polyurethanes of improved flame-resistance.

The manufacture of the solutions according to the invention, consisting of isocyanurate-polyisocyanates containing amide and/or acylurea groups in monomeric diisocyanates and/or polyisocyanates, can be subdivided into three steps, namely:

1. The manufacture of the diisocyanates and/or polyisocyanates containing amide and/or acylurea groups, which are used as starting materials for conversion to the isocyanurate.
2. The conversion of the diisocyanates and/or polyisocyanates containing amide and/or acylurea groups into the isocyanurate-polyisocyanates containing amide and/or acylurea groups by trimerization and, if appropriate, polymerization.
3. Mixing the products with monomeric diisocyanates and/or polyisocyanates which are free from amide, acylurea and isocyanurate groups.

The diisocyanates and/or polyisocyanates containing amide and/or acylurea groups are manufactured from polybasic carboxylic acids and diisocyanates and/or polyisocyanates by conventional methods, for example as described in Vieweg/Hochtlen, Kunststoffhandbuch, vol. VII, "Polyurethane," p. 79 (1966). Any polybasic carboxylic acid can be employed; specific examples are trimellitic acid, trimesic acid, mellitic acid and pyromellitic acid. However, optionally alkyl-substituted aliphatic dicarboxylic acids of 3 to 25 carbon atoms are preferred, and unsubstituted linear aliphatic dicarboxylic acids of 4 to 20 carbon atoms, e.g. succinic acid, glutaric acid, adipic acid, pimelic acid, suberic acid, sebacic acid, dodecanedicarboxylic acid and thapsic acid, are particularly preferred.

Isocyanates which can be used are aliphatic, cycloaliphatic, aliphatic-cycloaliphatic, araliphatic, cycloaliphatic-aliphaticaromatic and aromatic diisocyanates and/or polyisocyanates. In some cases it is desirable to add to the diisocyanates and/or polyisocyanates aliphatic, cycloaliphatic and/or aromatic monoisocyanates in amounts corresponding to from 0.01 to 0.5, preferably from 0.05 to 0.2 mole of monoisocyanate per mole of the diisocyanate and/or polyisocyanate in the isocyanate mixture. The diisocyanates and/or polyisocyanates containing amide and/or acylurea groups which have been produced in this way are of relatively low viscosity. Examples of suitable monoisocyanates are methylisocyanate, propylisocyanate, pentylisocyanate, cyclohexylisocyanate and phenylisocyanate. Examples of suitable diisocyanates are aliphatic diisocyanates, such as 1,6-hexamethylenediisocyanate, 1,10-decanediisocyanate and 1,12-dodecanediisocyanate, cycloaliphatic diisocyanates, such as 1,3- or 1,4-cyclohexanediisocyanate, 1-methylcyclohexane-2,4- and 2,6-diisocyanate and 3-isocyanatomethyl-3,5,5-trimethyl-cyclohexylisocyanate, araliphatic diisocyanates, such as cycloaliphatic-aliphatic-aromatic diisocyanates, e.g. 4-cyclohexyl-4'-phenylmethanediisocyanate, and aromatic diisocyanates, such as 1,3- and 1,4-phenylenediisocyanate, 2,4- and 2,6-toluylenediisocyanate, naphthalene-1,5-diisocyanate and 2,4'-, 2,2'- and/or 4,4'-diphenylmethanediisocyanate. Examples of suitable polyisocyanates are 2,4,6-toluylenetriisocyanate, triphenylmethane-4,4',4''-triisocyanate and the polyphenyl-polymethylenepolyisocyanates obtained by condensation of aniline and/or halogen-substituted or alkyl-substituted anilines with formaldehyde, followed by phosgenation. The diisocyanates and/or polyisocyanates can be used individually or as mixtures. The use of the commercially available products 2,4- and 2,6-toluylenediisocyanates or of mixtures consisting of these isomers, 4,4'-, 2,4'- and/or 2,2'-diphenylmethane-diisocyanate and polyphenyl-polymethylene-polyisocyanates or mixtures of these isocyanates is preferred.

To manufacture the polyisocyanates containing amide and/or acylurea groups, the diisocyanates and/or polyisocyanates and polybasic acids are reacted in amounts which correspond to a ratio of NCO to COOH groups of from 2 : 1 to 200 : 1, preferably from 20 to 100. The reaction takes place at industrially utilizable rates only at elevated temperatures; the reaction temperature and reaction time depend on the desired degree of conversion to the amide and/or acylurea. As a rule, temperatures of from 50° to 200°C, preferably of from 50° to 100°C, and reaction times of from 15 minutes to 2 ½ hours, preferably from 30 minutes to 2 hours, are required. The addition of certain tertiary amine catalysts, e.g. of 1,4-diazabicyclo(2,2,2)-octane, triethylamine, dimethylcyclohexylamine and N-methylmorpholine, has a particularly advantageous effect; even very low concentrations of these amines substantially accelerate the reaction. In general it suffices to use from 0.001 to 0.1% by weight, preferably from 0.01 to 0.06% by weight of the amine, based on the weight of polyisocyanate, at reaction temperatures of from 50° to 90°C.

The formation of amide- and/or acylurea-polyisocyanates can easily be followed, and controlled, by quantitatively determining the NCO content of the reaction batches, and by infrared spectroscopy. Amide- and/or acylurea-polyisocyanates have characteristic absorption bands at 1,680 and 1,720 cm$^{-1}$.

The diisocyanates and/or polyisocyanates containing amide and/or acylurea groups are then partially converted to isocyanurate-polyisocyanates containing amide and/or acylurea groups in a second reaction stage in the presence of a conventional trimerization catalyst, at reaction temperatures of from 50° to 150°C, preferably from 60° to 100°C.

The isocyanurate formation can be followed by quantitative determination of the NCO content of the reaction batches and by infrared spectroscopy until the chosen degree of trimerization or crosslinking is reached; in the infrared spectrum, the appearance of two intense bands at 1,700 – 1,710 cm$^{-1}$ and 1,400 – 1,410 cm$^{-1}$ is characteristic of the formation of the isocyanurate. The trimerizing or polymerizing action of the trimerization catalyst, which is preferably a basic catalyst, can be diminished or annulled, during the reaction, by adding acid compounds.

Examples of suitable trimerization catalysts are 1,3,5-tris-(3-dimethylaminopropyl)-hexahydrotriazine, 2,4,6-tri-(dimethylaminomethyl)-phenol, pyrrolizidine and tetramethylguanidine, and mixtures of these. The amount of trimerization catalyst to be used greatly depends on its reactivity which has been shown to depend on its basicity and its particular steric configuration. The amount used also depends on the desired degree of conversion to isocyanurate and on the reaction temperature used. At elevated temperatures, e.g. from 100° to 150°C, lower amounts of catalyst are used. In general, from 0.01 to 1% by weight, preferably from 0.1 to 0.5% by weight, of catalyst, based on the polyisocyanate containing amide and/or acylurea groups, is sufficient. Larger amounts of catalyst offer no advantages with regard to rate of reaction and degree of conversion to isocyanurate. The only effect they have is to require correspondingly larger amounts of acid compounds for stopping the trimerization or polymerization, and these compounds in turn may unneccessarily increase the acidity of the resulting isocyanurate-polyisocyanates containing amide and/or acylurea groups.

Acids or carboxylic acid halides are particularly suitable acid compounds for deactivating the trimerization catalyst. Examples are acids such as phosphoric acid and hydrogen chloride, and carboxylic acid halides such as acetyl chloride, benzoyl chloride and toluenesulfonyl chloride. In general, the isocyanurate formation is stopped effectively by adding approx. from 0.5 to 1 equivalent of acid and/or of carboxylic acid halide per equivalent of catalyst.

The conversion to isocyanurate can be carried out in the presence or absence of a solvent; in the former case, the solvent should not contain any hydrogen atoms which react with isocyanates. Suitable solvents are halogenated, aliphatic or aromatic hydrocarbons, e.g. methylene chloride, chloroform and chlorobenzene, ketones such as acetone and methyl ethyl ketone, esters such as ethyl acetate, and ethers such as tetrahydrofuran and dioxan. Where possible, however, the conversion to isocyanurate is carried out without using a solvent so as to avoid the expense of removing the solvent, e.g. by distillation.

The isocyanurate-polyisocyanates containing amide and/or acylurea groups which have been manufactured by the process of the invention contain from 26 to 0.25% by weight, preferably from 5 to 0.5% by weight, of amide and/or acylurea groups, from 29 to 5% by weight, preferably from 24 to 19% by weight, of isocyanurate groups, and from 40 to 20% by weight, preferably from 30 to 20% by weight, of free isocyanate groups, in each case based on the weight of isocyanurate-polyisocyanate containing amide and/or acylurea groups.

The isocyanurate-polyisocyanates containing amide and/or acylurea groups are then diluted with diisocyanates and/or polyisocyanates which are free from amide, acylurea and/or isocyanurate groups, to form the stable, liquid solutions according to the invention. Any diisocyanates and/or polyisocyanates which are liquid under normal conditions can be used as the monomeric isocyanates which are free from amide, acylurea and/or isocyanurate groups. Examples of suitable diisocyanates and/or polyisocyanates are hexamethylenediisocyanate m- and p-xylylenediisocyanate and cyclohexane-1,3- and 1,4-diisocyanate. However, 2,4- and 2,6-toluylenediisocyanate or their commercially available mixtures, and mixtures of diphenylmethanediisocyanates and polyphenylpolymethylene-polyisocyanates are preferred.

The isocyanurate-polyisocyanates containing amide and/or acylurea groups are diluted with sufficient monomeric diisocyanates and/or polyisocyanates which are free from isocyanurate groups to give stable, liquid solutions according to the invention which contain from 5 to 40% by weight, preferably from 10 to 30% by weight, of an isocyanurate-polyisocyanate containing amide and/or acylurea groups and from 95 to 60% by weight, preferably from 90 to 70% by weight, of a monomeric diisocyanate and/or polyisocyanate which is free from isocyanurate groups.

The dilution is generally carried out at temperatures below 100°C.

The stable, liquid solutions according to the invention, which contain isocyanurate-polyisocyanates containing amide and/or acylurea groups can be used to manufacture polyurethanes. They are particularly suitable for the manufacture of polyurethane surface coatings, polyurethane adhesives and polyurethane foams of increased load-bearing capacity and improved flame-resistance.

The parts in the examples which follow are parts by weight.

EXAMPLE 1

18.9 parts of adipic acid and 0.2 part of 1,4-diazabicyclo-(2,2,2)-octane are added to 451 parts of toluylenediisocyanate, consisting of 80% by weight of 2,4-toluylenediisocyanate and 20% by weight of 2,6-toluylenediisocyanate, whilst stirring. The mixture is heated to 80°C in the course of one hour, whilst stirring, and then has an NCO content of 43.5% (calculated NCO content after complete conversion: 42.6%). The reaction mixture is then cooled to from 30° to 40°C, one part of pyrrolizidine is added and the batch is heated to 110°C in the course of 45 minutes. The NCO content then found is 27.5% and the isocyanurate-polyisocyanate mixture still contains 35% of free toluylenediisocyanate. The conversion to isocyanurate is now stopped by adding 2.2 parts of benzoyl chloride and the reaction mixture is cooled to 90°C and then diluted with 800 parts of a mixture of 2,4-toluylenediisocyanate and 2,6-toluylenediisocyanate in the weight ratio of 80 : 20. The stable, liquid solution of isocyanurate-polyisocyanates containing amide and acylurea groups in monomeric toluylenediisocyanate gives the following values:

NCO content 40.7%; viscosity at 25°C: 37 cp; free toluylenediisocyanate: 72.5%.

The table which follows shows that the product is stable on storage.

| Length of storage | % NCO | Viscosity (25°) in cp | Condition of the product |
| --- | --- | --- | --- |
| 1 week | 40.5 | 38 | Clear solution |
| 1 month | 40.1 | 39 | Clear solution |
| 2 months | 40.0 | 40 | Clear solution |
| 3 months | 40.1 | 40 | Clear solution |
| 4 months | 40.0 | 42 | Clear solution |

EXAMPLE 2

6 parts of adipic acid and 0.2 part of 1,4-diazabicyclo-(2,2,2)-octane are added to 444 parts of toluylenediisocyanate, consisting of 80% by weight of 2,4-toluylenediisocyanate and 20% by weight of 2,6-toluylenediisocyanate, whilst stirring. The mixture is heated to 80°C in the course of one hour and 40 minutes and then has an NCO content of 46.8% (calculated NCO content after complete conversion: 46.8%). After adding one part of pyrrolizidine, the reaction mixture is heated to 90°C in the course of one hour, during which its NCO content decreases to 25.8%. The conversion to isocyanurate is stopped by adding 2.2 parts of benzoyl chloride and the reaction mixture is diluted with 815 parts of 2,4-toluylenediisocyanate and 2,6-toluylenediisocyanate in the weight ratio of 80 : 20. After cooling to room temperature, the mixture is a clear stable solution which gives the following values:

NCO content: 40.7%, viscosity at 25°C: 36 cp; free toluylenediisocyanate: 73.1%.

The table which follows shows that the product is stable on storage.

| Length of storage | % NCO | Viscosity (25°) in cp | Condition of the product |
|---|---|---|---|
| 1 week | 40.6 | 36 | Clear solution |
| 1 month | 40.1 | 39 | Clear solution |
| 2 months | 40.1 | 38 | Clear solution |
| 3 months | 40.0 | 39 | Clear solution |
| 4 months | 39.9 | 39 | Clear solution |

EXAMPLE 3

By following an analogous procedure to Example 2, but using 400 parts of a mixture of 2,4-toluylenediisocyanate and 2,6-toluylenediisocyanate in the weight ratio of 80 : 20, 19.1 parts of o-phthalic acid and 0.2 part of 1,4-diazabicyclo-(2,2,2)-octane, a reaction mixture with an NCO content of 46.4% is obtained (calculated NCO content after complete conversion 46.5%). After addition of one part of pyrrolizidine at from 30° to 40°C, the reaction mixture is heated to 80°C in the course of 45 minutes, during which the NCO content decreases to 24.9%. The conversion to isocyanurate is stopped by adding 2.2 parts of benzoyl chloride and the reaction mixture is diluted with 770 parts of monomeric 2,4-toluylenediisocyanate and 2,6-toluylenediisocyanate in the weight ratio of 80 : 20. After cooling to room temperature, the mixture is a clear stable solution which gives the following values:

NCO content: 40.2%, viscosity at 25°C: 147 cp; free toluylenediisocyanate: 71.5%.

The solution remains clear over a period of observation of 4 months.

EXAMPLE 4

49.2 parts of adipic acid and 0.2 part of 1,4-diazabicyclo-(2,2,2)-octane are added to 283 parts of hexamethylene-diisocyanate, whilst stirring, and the reaction mixture is heated to 100°C over the course of 2.5 hours, during which the NCO content decreases to 34.0% (calculated NCO content after complete conversion 32.5%). The reaction mixture is cooled to 30°C, 117 parts of 2,4-toluylenediisocyanate and 2,6-toluylenediisocyanate (weight ratio 80 : 20) and one part of 1,3,5-tris-(3-dimethylaminopropyl)-hexahydrotriazine are added and the batch is then stirred for 2 hours at 90°C, during which the NCO content decreases to 27.1%. The conversion to isocyanurate is then stopped by adding 3.04 parts of benzoyl chloride and the reaction mixture is diluted with 670 parts of 2,4-toluylenediisocyanate and 2,6-toluylenediisocyanate (weight ratio 80 : 20). A clear stable solution having an NCO content of 40.0% and a viscosity of 35 cp at 25°C is obtained.

The table which follows shows that the product is stable on storage.

| Length of storage | % NCO | Viscosity (25°) in cp | Condition of the product |
|---|---|---|---|
| 1 week | 40.1 | 35 | Clear solution |
| 1 month | 39.9 | 37 | Clear solution |
| 2 months | 39.8 | 38 | Clear solution |
| 3 months | 39.9 | 38 | Clear solution |
| 4 months | 39.7 | 38 | Clear solution |

EXAMPLE 5

A mixture of 250 parts of 4,4'-diisocyanatodiphenylmethane and 14.6 parts of adipic acid is heated to 80°C in one hour, and then has an NCO content of 28.9% (calculated NCO content after complete conversion: 28.6%). The reaction mixture is cooled to 50°C, 0.65 part of pyrrolizidine is added and the batch is then heated to 80°C in the course of 45 minutes. The NCO content of the mixture is then 23.2%. The conversion to isocyanurate is then stopped by adding 0.83 part of benzoyl chloride and the reaction mixture is diluted with 555 parts of 2,4-toluylenediisocyanate and 2,6-toluylenediisocyanate in the weight ratio of 80 : 20. The solution is clear and stable at room temperature and has an NCO content of 40.5% by weight.

EXAMPLE 6

250 parts of 4,4'-diphenylmethanediisocyanate are liquefied by heating to 40°C and 14.6 parts of adipic acid are added. The mixture is then heated, whilst stirring, to 85°C in the course of 2 hours, during which the NCO content decreases to 29.2% (calculated NCO content on complete conversion: 28.6%). The reaction mixture is cooled to 50°C, 0.65 part of pyrrolizidine is added and the batch is heated to 60°C in the course of one hour. The reaction mixture then has an NCO content of 23%. The conversion to isocyanurate is now stopped by adding 0.85 part of benzoyl chloride and the very viscous mixture is diluted with 4,340 parts of polyphenyl-polymethylenepolyisocyanate having an NCO content of 31.2% and a viscosity of 206. Heating the reaction mixture to 150°C in the course of one hour gives a clear, homogeneous solution with an NCO content of 28.5% and a viscosity of 616 cp at 25°C. The table which follows shows that the clear homogeneous solution is stable on storage at room temperature.

| Length of storage | % NCO | Viscosity (25°) in cp | Condition of the product |
|---|---|---|---|
|  | 28.5 | 616 | No detectable turbidity |
| 1 week | 28.3 | 620 | " |
| 2 weeks | 28.2 | 625 | " |
| 1 month | 28.3 | 623 | " |
| 2 months | 28.2 | 621 | " |
| 3 months | 28.3 | 625 | " |
| 4 months | 28.4 | 625 | " |

EXAMPLE 7

19.3 parts of sebacic acid and 0.2 part of 1,4-diazabicyclo-(2,2,2)-octane are added, whilst stirring, to 400 parts of toluylenediisocyanate, consisting of 80% by weight of 2,4-toluylenediisocyanate and 20% by weight of 2,6-toluylenediisocyanate. The mixture is heated to 95°C in the course of 70 minutes and then has an NCO content of 43.4% (calculated NCO content after complete conversion to the amide: 44.9%; calculated NCO content after complete conversion to the acylurea: 42.9%). The reaction mixture is then cooled to from 30° to 40°C, one part of pyrrolizidine is added and the batch is then heated to 100°C in 30 minutes, during which the NCO content of the reaction mixture decreases to 27.1%. The content of free toluylenediisocyanate is 28%. The conversion to isocyanurate is stopped by adding 2.2 parts of benzoyl chloride and the reaction mixture is diluted with 626 parts of 2,4-toluylenediisocyanate and 2,6-toluylenediisocyanate in the weight ratio of 80 : 20. After cooling to room temperature, the solution is clear and gives the following values:

NCO content: 40.4%; viscosity at 25°C: 57 cp; free toluylenediisocyanate: 72.5%.

The table which follows shows that the product is stable on storage:

| Length of storage | % NCO | Viscosity (25°) in cp | Condition of the product |
|---|---|---|---|
| 1 week | 40.0 | 58 | Clear solution |
| 1 month | 39.7 | 59 | Clear solution |
| 2 months | 39.5 | 60 | Clear solution |
| 3 months | 39.5 | 60 | Clear solution |
| 4 months | 39.6 | 60 | Clear solution |

EXAMPLE 8

31.4 parts of heptadecanedicarboxylic acid and 0.2 part of 1,4-diazabicyclo-(2,2,2)-octane are added, whilst stirring, to 400 parts of toluylenediisocyanate, consisting of 80% by weight of 2,4-toluylenediisocyanate and 20% by weight of 2,6-toluylenediisocyanate. The mixture is heated to 40°C in the course of 75 minutes and then has an NCO content of 42.0% (calculated NCO content after complete conversion to the amide: 43.7%; calculated NCO content after complete conversion to the acylurea: 41%). One part of pyrrolizidine is added and the reaction mixture is heated to 80°C in 50 minutes, during which its NCO content decreases to 26.0%. The conversion to isocyanurate is stopped by adding 2.2 parts of benzoyl chloride and the reaction mixture is diluted with 675 parts of a mixture of 2,4-toluylenediisocyanate and 2,6-toluylenediisocyanate. The solution obtained after cooling is clear and stable on storage over a period of observation of 4 months, and gives the following values:

NCO content: 40%, viscosity at 25°C: 45 cp; free toluylenediisocyanate: 77.3%.

COMPARATIVE EXAMPLE 1

0.2 part of 1,3,5-tris-(3-dimethylaminopropyl)-hexahydrotriazine is added to 100 parts of one of the following mixtures of 2,4-toluylenediisocyanate and 2,6-toluylenediisocyanate:

a) 95% of 2,4-toluylenediisocyanate and 5% of 2,6-toluylenediisocyanate
b) 90% of 2,4-toluylenediisocyanate and 10% of 2,6-toluylenediisocyanate
c) 80% of 2,4-toluylenediisocyanate and 20% of 2,6-toluylenediisocyanate
d) 65% of 2,4-toluylenediisocyanate and 35% of 2,6-toluylenediisocyanate
e) 50% of 2,4-toluylenediisocyanate and 50% of 2,6-toluylenediisocyanate at 20° to 30°C, whilst stirring. The exothermic isocyanurate formation commences immediately and the temperature rises to from 130° to 140°C in the course of from 2 to 5 minutes. The reaction mixture is now cooled to 100°C and stirred at this temperature until (after about 1.5 hours) the original NCO content of 48.3% has decreased to 25.4%. The trimerization is now stopped with 0.48 part of benzoyl chloride. 195 parts of 2,4-toluylenediisocyanate and 2,6-toluylenediisocyanate in the weight ratio of 80 : 20 are added to the very viscous reaction product, and on stirring at 80°C a clear solution having an NCO content of 40.5% is obtained. After the solutions have been cooled to from 20° to 25°C, they all deposit fine crystalline solids in the course of from 1 to 14 days; the amount of solids increases with increasing content of 2,6-toluylenediisocyanate in the toluylenediisocyanate isomer mixtures shown under a to e.

COMPARATIVE EXAMPLE 2

0.65 part of pyrrolizidine is added to 250 parts of 4,4'-diphenylmethanediisocyanate which has been fused at 40°C; the mixture is heated, whilst stirring, to 80°C in the course of 45 minutes and is stirred at this temperature for a further 15 minutes. The reaction product, which has an NCO content of 24.6%, is diluted with 500 parts of 2,4-toluylenediisocyanate and 2,6-toluylenediisocyanate in the weight ratio of 80 : 20 and the batch is again stirred, for 3 hours at 90°C. This causes only a part of the isocyanurate mixture to dissolve in the monomeric toluylenediisocyanate. The remainder continues undissolved even at temperatures up to 120°C.

COMPARATIVE EXAMPLE 3

56.6 parts of a mixture of 71% by weight of dipropylene glycol, 24% by weight of tripropylene glycol and 2.5% by weight of tetrapropylene glycol are added dropwise in the course of 2 hours, whilst stirring, to 591 parts of toluylenediisocyanate, consisting of 80% by weight of 2,4-toluylenediisocyanate and 20% by weight of 2,6-toluylenediisocyanate; the reaction mixture reaches a maximum temperature of 40°C without external application of heat. The mixture obtained has an NCO content of 39.2% (calculated value after complete conversion to the urethane: 39.3%). 0.2 part of pyrrolizidine is added and the mixture is then heated to 70°C in the course of 1 ½ hours, during which the NCO content decreases to 27.9%. The mixture of isocyanurates containing urethane groups still contains 45.5% by weight of free toluylenediisocyanate. The formation of isocyanurate is then stopped by adding 0.5 part of benzoyl chloride and the reaction mixture is diluted with 957 parts of a mixture of 2,4-toluylenediisocyanate and 2,6-toluylenediisocyanate, and is stirred at 80°C until a clear solution forms. The reaction mixture gives the following values:

NCO content: 40.0%; viscosity at 25°C: 25 cp; free toluylenediisocyanate: 78%.

The reaction mixture becomes turbid after 5 days' storage at from 20° to 25°C and deposits substantial amounts of fine crystalline solid after 10 days.

We claim:

1. Stable, liquid solutions of isocyanurate-polyisocyanates containing amide and/or acylurea groups, which solutions contain:

A. From 5 to 40% by weight, based on the total weight of solution, of an isocyanurate-polyisocyanate with amide and/or acylurea groups, containing from 26 to 0.25% by weight of amide and/or acylurea groups, from 29 to 5% by weight of isocyanurate groups and from 40 to 20% by weight of free isocyanate groups, in each case based on the weight of the isocyanurate-polyisocyanate containing amide and/or acylurea groups, and B. from 95 to 60% by weight, based on the total weight of the solution, of a monomeric diisocyanate and/or polyisocyanate which is free from isocyanurate groups.

2. Stable, liquid solutions of isocyanurate-polyisocyanates containing amide and/or acylurea groups, which solutions consist of:
A. From 5 to 40% by weight, based on the total weight of solution, of an isocyanurate-polyisocyanate with amide and/or acylurea groups, containing from 26 to 0.25% by weight of amide and/or acylurea groups, from 29 to 5% by weight of isocyanurate groups and from 40 to 20% by weight of free isocyanate groups, in each case based on the weight of the isocyanurate-polyisocyanate containing amide and/or acylurea groups, and
B. from 95 to 60% by weight, based on the total weight of the solution, of a monomeric diisocyanate and/or polyisocyanate which is free from isocyanurate groups.

3. A process for the production of stable, liquid solutions of isocyanurate-polyisocyanates containing amide and/or acylurea groups, wherein monomeric organic diisocyanates and/or polyisocyanates are reacted in a first step with aliphatic and/or aromatic dicarboxylic acids of 4 to 20 carbon atoms used in such amounts that the ratio of NCO to COOH groups is from 200:1 to 2:1, the resulting diisocyanates and/or polyisocyanates containing amide and/or acylurea groups are partially trimerized and/or polymerized in a second step in the presence of a trimerization catalyst and after deactivation of the trimerization catalyst the resulting isocyanurate-polyisocyanates containing amide and/or acylurea groups are diluted in a third step with monomeric diisocyanates and/or polyisocyanates which are free from isocyanurate groups.

4. A process for the production of stable, liquid solutions of isocyanurate-polyisocyanates containing amide and/or acylurea groups, as claimed in claim 3, wherein the isocyanates used are aliphatic and/or aromatic diisocyanates and/or polyisocyanates.

5. A process for the production of stable, liquid solutions of isocyanurate-polyisocyanates containing amide and/or acylurea groups, as claimed in claim 4, wherein the aromatic diisocyanates and/or polyisocyanates used are 2,4-toluylenediisocyanate, 2,6-toluylenediisocyanate, 4,4'- or 2,4'-diphenylmethane-diisocyanate and polyphenyl-polymethylene-polyisocyanates, or mixtures of the said compounds.

6. A process for the production of stable, liquid solutions of isocyanurate-polyisocyanates containing amide and/or acylurea groups, as claimed in claim 3, wherein the diisocyanates and/or polyisocyanates, containing amide and/or acylurea groups, which are converted to isocyanurates, are prepared in the presence of aliphatic and/or aromatic monoisocyantes.

7. A process for the production of stable, liquid solutions of isocyanurate-polyisocyanates containing amide and/or acylurea groups, as claimed in claim 6, wherein said aliphatic and/or aromatic monoisocyanates are selected from the group consisting of methyl isocyanate, ethyl isocyanate, propyl isocyanate, pentyl isocyanate and phenyl isocyanate.

* * * * *